US006275718B1

(12) United States Patent
Lempert (10) Patent No.: US 6,275,718 B1
(45) Date of Patent: Aug. 14, 2001

(54) METHOD AND APPARATUS FOR IMAGING AND ANALYSIS OF OCULAR TISSUE (76) Inventor: Philip Lempert, 200 E. Buffalo St., Ithaca, NY (US) 14850

( * ) Notice: Subject to any disclaimer, the term of this patent is extended or adjusted under 35 U.S.C. 154(b) by 0 days.

(21) Appl. No.: 09/274,203

(22) Filed: Mar. 23, 1999

(51) Int. Cl.[7] .................................................. A61B 3/10
(52) U.S. Cl. ........................ 600/407; 600/476; 351/219
(58) Field of Search ................................. 600/407, 109, 600/131, 108, 112, 122, 176, 178, 213, 234, 465, 472–476; 606/46; 351/219, 206, 205, 218

(56) References Cited

U.S. PATENT DOCUMENTS

| 4,213,678 | * | 7/1980 | Pomerantzeff et al. | 351/206 |
|---|---|---|---|---|
| 4,838,679 | * | 6/1989 | Bille | 351/205 |
| 5,042,939 | * | 8/1991 | Zayek | 351/206 |
| 5,125,730 | | 6/1992 | Taylor . | |
| 5,139,022 | | 8/1992 | Lempert . | |
| 5,146,463 | | 9/1992 | Rando . | |
| 5,227,910 | | 7/1993 | Khattak . | |
| 5,404,884 | | 4/1995 | Lempert . | |
| 5,423,312 | * | 6/1995 | Siegmund et al. | 600/109 |
| 5,450,144 | * | 9/1995 | Nun | 351/219 |
| 5,470,329 | | 11/1995 | Sumiya . | |
| 5,488,443 | | 1/1996 | Ota et al. . | |
| 5,507,799 | | 4/1996 | Sumiya . | |
| 5,549,599 | | 8/1996 | Sumiya . | |
| 5,562,656 | | 10/1996 | Sumiya . | |
| 5,596,377 | | 1/1997 | Yano . | |
| 5,620,437 | | 4/1997 | Sumiya . | |
| 5,624,436 | | 4/1997 | Nakamura . | |
| 5,634,249 | | 6/1997 | Ballarati . | |
| 5,637,109 | | 6/1997 | Sumiya . | |
| 5,684,562 | | 11/1997 | Fujieda . | |
| 5,685,877 | * | 11/1997 | Pagedas et al. | 606/46 |
| 5,706,072 | | 1/1998 | Kawamura . | |
| 5,726,735 | | 3/1998 | Kawamura . | |
| 5,784,146 | | 7/1998 | Nanjo et al. . | |
| 5,785,644 | * | 7/1998 | Grabover et al. | 600/131 |
| 5,800,424 | | 9/1998 | Sumiya . | |
| 5,817,088 | | 10/1998 | Sterling . | |
| 5,861,939 | | 1/1999 | Heacock . | |
| 5,993,378 | * | 11/1999 | Lemelson | 600/109 |

FOREIGN PATENT DOCUMENTS

| PCT/US90/ 00724 A1 | 8/1990 | (WO) . |
|---|---|---|
| PCT/US91/ 08003 A1 | 5/1992 | (WO) . |
| PCT/US95/ 02548 A1 | 9/1995 | (WO) . |

OTHER PUBLICATIONS

European Search Report, Aug. 24, 2000.

* cited by examiner

Primary Examiner—Teresa Walberg
Assistant Examiner—Quang Van
(74) Attorney, Agent, or Firm—Hopgood, Calimafde, Judlowe & Mondolino LLP (57) ABSTRACT A method and accompanying apparatus are provided for in vivo imaging of corneal tissue which, in general, includes a laser beam having a substantially planer configuration so as to illuminate the cross-sectional portion of a patient's eye and cause the laser beam to be scattered by molecules in the corneal tissue. The scattered laser light is detected to form a cross-sectional image of the corneal tissue. Corneal thickness and topographical data can be produced for use by ophthalmological surgeons in planning the precise curvature profile that must be photo-ablatively sculptured in the stroma tissue of a particular patient in order to achieve a desired degree of optical correction in his or her eye. Additionally disclosed is a miniaturized apparatus for use in the field which includes a housing having a laser source for illuminating the patient's eye and a camera for recording the reflected light and one of (a) a controlled moving target for the patient's eye under examination to focus upon (e.g., a series of lamps) or (b) a device for scanning the beam (e.g., a prism or piezo- or electooptical crystal).

17 Claims, 9 Drawing Sheets

METHOD AND APPARATUS FOR IMAGING AND ANALYSIS OF OCULAR TISSUE

BACKGROUND OF INVENTION

1. Field of Invention

The present invention generally relates to a method and apparatus for objectively assessing in vivo the properties of ocular tissue, and more particularly to a method and apparatus for in vivo imaging and analysis of corneal tissue in an objective and quantitative manner for diagnostic and therapeutic purposes.

2. The State of the Art

In many diagnostic and therapeutic applications, there is great need to objectively quantify the optical density, shape and size of various ocular tissue, such as the crystalline lens and cornea.

Regarding the cornea lens, it is well known that the presence of corneal haze at particular locations on the cornea can effect, in particular individuals, the visual acuity and function of the eye. It is also known that the optical density of the corneal haze is related to the amount of light diffusion (ie., scatter) caused by increased size and coagulation of protein molecules in the cornea. Presently, prior art descriptions of corneal haze have generally consisted of a morphologic statement. Such morphologic descriptions have been based primarily on the patient's potential visual acuity estimated using an acuity scope.

A number of techniques have been developed over recent years for achieving desired refraction-corrective surgery in the human eye by laser sculpturing the optically used portion of the cornea. Examples of such prior art techniques are disclosed in U.S. Pat. Nos. 4,718,418; 4,732,148; 4,773,414; 4,729,372; 4,669,466; 4,473,330; 4,856,513; and 4,994,058. While some of these U.S. Letters patents utilize different forms of apparatus, they each disclose essentially the same method for photoablative laser sculpture of the cornea.

In general, the preoperative step of the method involves removing the epithelial layer from central anterior area of the cornea. Then an ultraviolet laser beam of a controlled cross-sectional diameter is directed to the epithelium free area for uniform photoablation through the Bowman's membrane and selective penetration of the stroma, achieving a new curative profile of predetermined characteristics solely in stroma tissue. Thereafter, post operative procedures favorable to smooth efficient epithelial regrowth over the surgically sculptured region are performed. As it is not presently uncommon for a certain amount of corneal "haze" or light scattering to result from the laser sculpturing procedure, which may be more or less noticeable in different patients, post-operative treatment of this disorder is also typically performed using a variety of typically applied drugs.

Prior to performing the corneal sculpturing procedure described above, it is important to acquire data representative of thickness and topography of the cornea of a particular abnormal eye. Such data must be in the form of a readily interpretable context against which the depth and surface distribution of the surgical incision into the anterior surface of the abnormal cornea can be determined in order to achieve a desired refractive correction in the patient's eye. In addition, for medical and legal documentation purposes, it is important for the ophthalmological surgeon to objectively determine and record the precise degree of corneal haze present in the patient's eye prior to and after laser sculpture of the cornea.

U.S. Pat. No. 4,669,466 discloses a CAD/CAM system for use in acquiring corneal topographical and thickness data which can be used by the ophthalmological surgeon in determining the new curvature profile to be formed in the stroma in order to achieve a desired degree of optical correction in the patient's eye. Equipment presently used for acquiring corneal topographical data includes an optical ocular scanner or a photokeratometer with provision for generating digitized topographical data. Exemplary of this equipment is the PFS-1000 photokeratoscope commercially available from the Japanese firm, Sun Contact Lens Co., Ltd., with U.S. offices in Palo Alto, Calif. The Sun photokeratoscope has the ability to rapidly scan the cornea in such a way as to determine the entire topography of the outer surface of the cornea, from limbus to limbus. Subtle differences in curvature of the outer cornea or inner optical zone are precisely and clearly defined. The photokeratoscope is available with a photoanalyzer having the capability of digitizing the data from thousands of individual points on the particular cornea, and producing a digitized output, from which a visual display is producible to show the cross-sectional profile of anterior-surface curvature for any cross-sections which include the central axis of the eye.

Equipment presently used for acquiring corneal thickness data includes pachymeter for making multiple determinations of the precise thickness of the cornea, to within thousandths of a millimeter, at plural locations on the surface of the cornea. Using ultrasonic-ranging, measured thickness data correlated with location-coordinate data is provided as digitized output. The pachymeter measurements may be performed manually on an individual point-by-point basis, using a commercially available hand-held transducer probe flexibly connected to power supply and display means, for example the Myopach ultrasonic pachymeter available from Myocure, Inc., Los Angeles, Calif., or the "Villasenor" ultrasonic pachymeter, available from Cilco, Inc. Huntington, W. Va. In using such a device, a fixation target enables the unexamined eye of the patient to maintain central-axis stability for his examined eye when the probe is placed on the corneal surface anywhere from the central optical axis to the periphery.

Various patents that describe apparatus for measuring ocular tissue are described in the following U.S. Pat. Nos.: 5,684,562; 5,634,249; 5,673,109; 5,624,436; 5,620,437; 5,470,329; 5,596,377; 5,562,656; 5,507,799; 5,549,599; 5,488,443; 5,139,022; 5,404,884; 5,800,424; 5,784,146; 5,817,088; 5,726,735; and 5,706,072; the disclosures of which are incorporated herein by reference.

While the above-described equipment has the capability of acquiring topographical and thickness data of the cornea, the nature of this data is approximate as it has been generated on the basis of a fixed number of measurements made at points along the surface of the cornea and then applying mathematical estimation techniques.

Thus, there is great need for a method and apparatus that is capable of producing objective measurements of corneal haze and determining the 3-D geometry of the cornea and associated structures in a way which is free from the shortcomings and drawbacks accompanying the prior art.

Accordingly, it is primary object of the present invention to provide a method and apparatus for in vivo imaging and analysis of corneal tissue in an objective, quantitative manner.

It is a further object of the present invention to provide such a method and apparatus, from which cross-sectional images of corneal tissue can be formed over a high depth of field extending far beyond the thickness of the cornea and crystalline lens.

A further object of the present invention is to provide such a method and apparatus, from which accurate cross-sectional images of corneal tissue can be formed, with correct spatial relationships between ocular structures.

A further object of the present invention is to provide a method and apparatus for precisely measuring the physical dimensions of the cornea and its correct spatial relationships within the eye.

An even further object of the present invention is to provide a method and apparatus for forming cross-sectional images of corneal tissue which enable precise localization of zones of increased optical density, such as corneal haze.

Yet a further object of the present invention is to provide a laser-based corneal tissue analysis system in which cross-sectional digital images of the cornea, crystalline lens and surrounding ocular structures can be formed and from which the precise degree and location of optical density of the cornea can be objectively determined using digital image analysis.

A further object of the present invention is to provide such a corneal tissue analysis system in which the luminance and cross-sectional dimension of the laser illumination used to visualize the lens and form cross-sectional corneal images, can be maintained essentially uniformly constant from image to image, and photo-examination session to photo-examination session.

A further object of the present invention is to provide such a corneal tissue analyzing system which includes a microscope and an image detector that uses laser illumination for visualizing and forming perfectly focused cross-sectional images entirely through the outer tissue comprising the cornea and crystalline lens.

An even further object of the present invention is to provide a laser-based corneal tissue analysis system in which 3-D model of the cornea and its surrounding ocular structures in the eye can be generated using cross-sectional digital images formed of these structures.

These and other objects of invention will become apparent hereinafter and in the claims.

SUMMARY OF INVENTION

According to one of broader aspects of the present invention, a method and accompanying apparatus are provided for in vivo imaging of corneal tissue. In general, the method comprises providing a laser beam having a substantially planer configuration. The planar laser beam is directed through a cross-sectional portion of the corneal tissue, so as to illuminate the cross-sectional portion and cause the laser beam to be scattered by molecules in the corneal tissue. Then, at least a portion of the scattered laser light is detected so as to form a cross-sectional image of the corneal tissue. In general, the planar configured laser beam has a slit-like cross-sectional dimension having substantially the same width dimension over the depth of field within which the largest depth dimension of the eye extends. These unique characteristics of the illumination beam permit the formation of clear, in-focus images detected at the image detection plane. The method and apparatus of the present invention can be used for objectively measuring the optical density of ocular tissue, as well as precisely measuring the physical dimension of ocular structures and their correct spatial relationships within the eye. In the case of the cornea, the method and apparatus of the present invention can be utilized to produce in-focus cross-sectional images, from which the optical density of tissue forming the cornea can be precisely measured and thus the precise degree of and location of corneal haze therewithin determined. In the case of the crystalline lens, the method and apparatus of the present invention can be utilized to produce in-focus cross-sectional images, from which the optical density of tissue comprising the lens can be precisely measured and thus the precise degree and location of cataract therewithin determined. In the illustrated embodiment, the apparatus of the present invention is realized in the form of an ocular tissue analysis system, which is capable of forming a plurality of cross-sectional images of the corneal tissue, with each image being specified at a different light scatter plane, defined within the corneal tissue. Preferably, the corneal tissue analysis system comprises illumination beam directing means for directing the planar laser beam into the ocular tissue at a selected angle of incidence with respect to the corneal tissue, so that, for each selected angle of incidence, the laser light scatters principally in a different light scatter plane within the corneal tissue. The system also includes detecting means for detecting a portion of the scattered laser light from each different light scatter plane. On the basis of the plurality of acquired cross-sectional images, a three-dimensional image or model of the corneal tissue can be reconstructed and subsequently displayed along desired viewing directions. From the three-dimensional image model of the cornea, the physical thickness of the cornea can be accurately determined at each point along the surface of the cornea. Also, from the three-dimensional image model of the cornea, its topography (ie., surface characteristics) can be accurately determined. Corneal thickness and topographical data (i.e., corneal curvature) obtained from the three-dimensional image model of the cornea can then be used by the ophthalmological surgeon in planning the precise curvature profile that must be photoablatively sculptured in the stroma tissue of a particular patient in order to achieve a desired degree of optical correction in his or her eye.

BRIEF DESCRIPTION OF THE DRAWINGS

For a further understanding of the objects of the present invention, the detailed description of the illustrated embodiment is to be taken in connection with the following drawings, wherein.

DETAILED DESCRIPTION OF ILLUSTRATED EMBODIMENTS

Figure 1A:
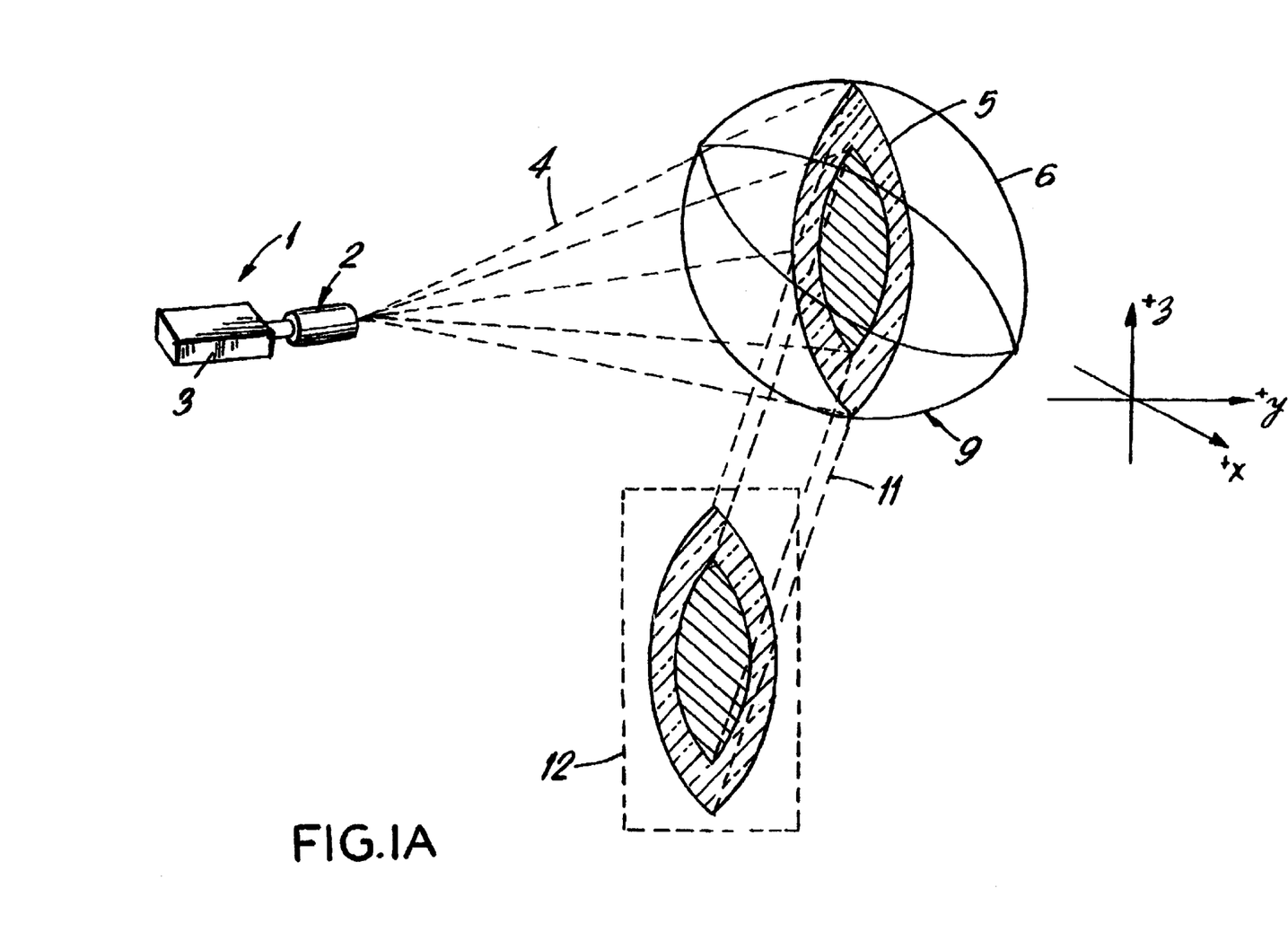
FIG. 1A is a schematic representation of the method of image formation according to the present invention, showing the illumination of a cross-sectional portion of a crystalline lens with a substantially uniform planar laser beam of substantially uniform luminance and the detection of scattered laser light from the cross-sectional portion to form an image thereof at the image detection plane.
Figure 1B:
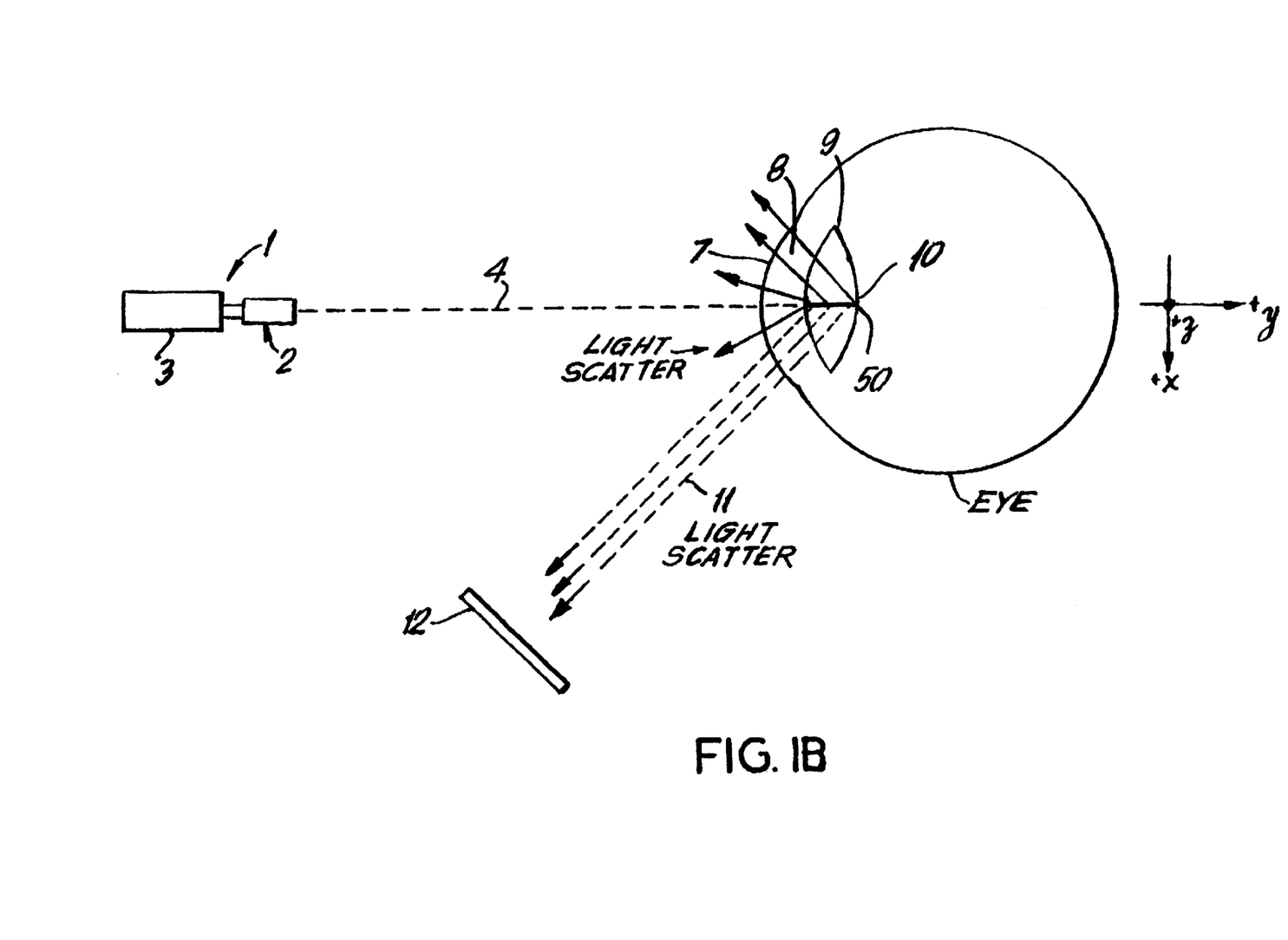
FIG. 1B is a schematic representation of the method of the present invention, illustrating the path of laser illumination and light scatter and detection, as viewed from along the Z-Y plane of the coordinate reference system of FIG. 1A.
Figure 2:
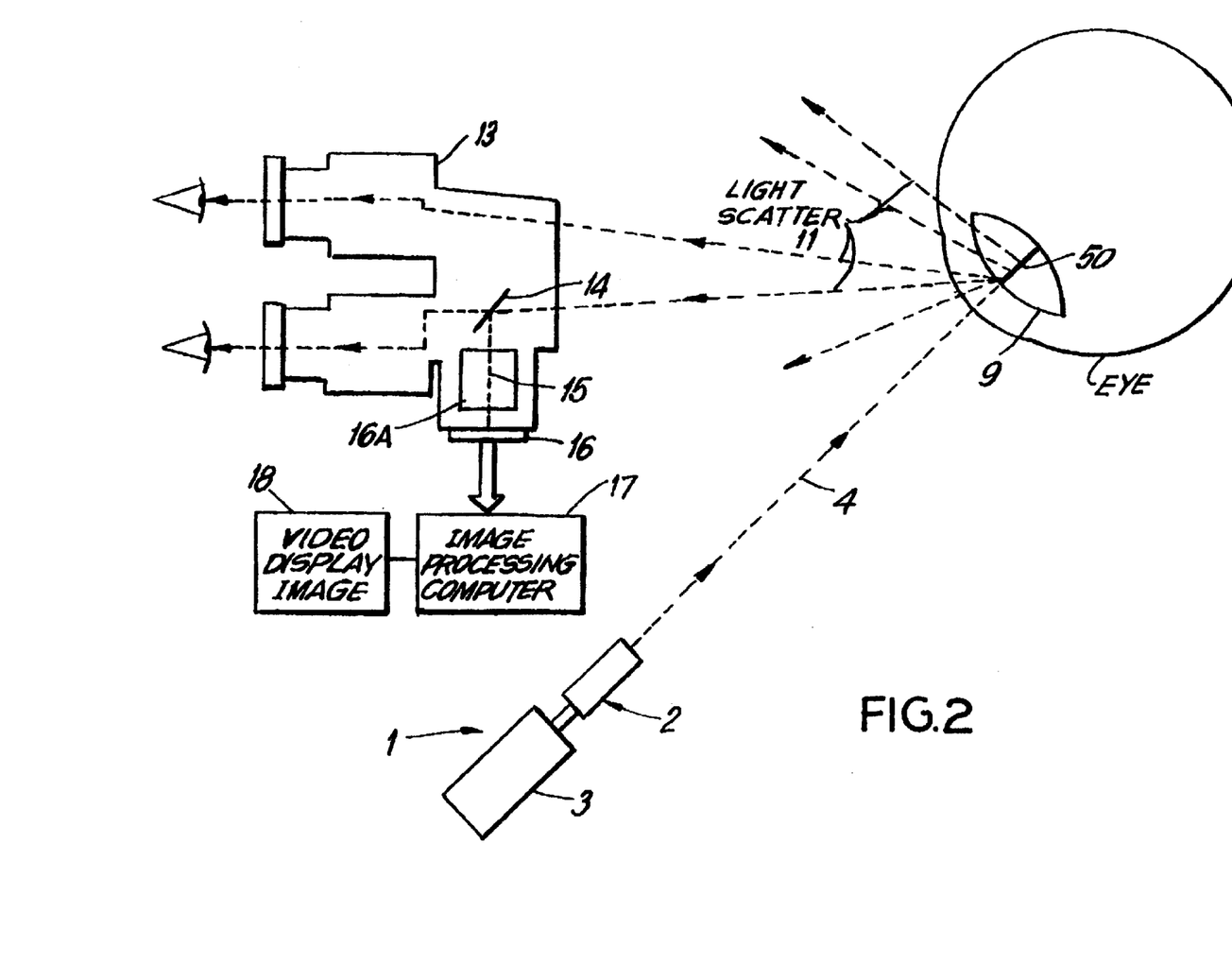
FIG. 2 is a schematic representation of the first embodiment of the present invention realized as a binocular microscopic and scatter image detection and analysis system.
Figure 3A:
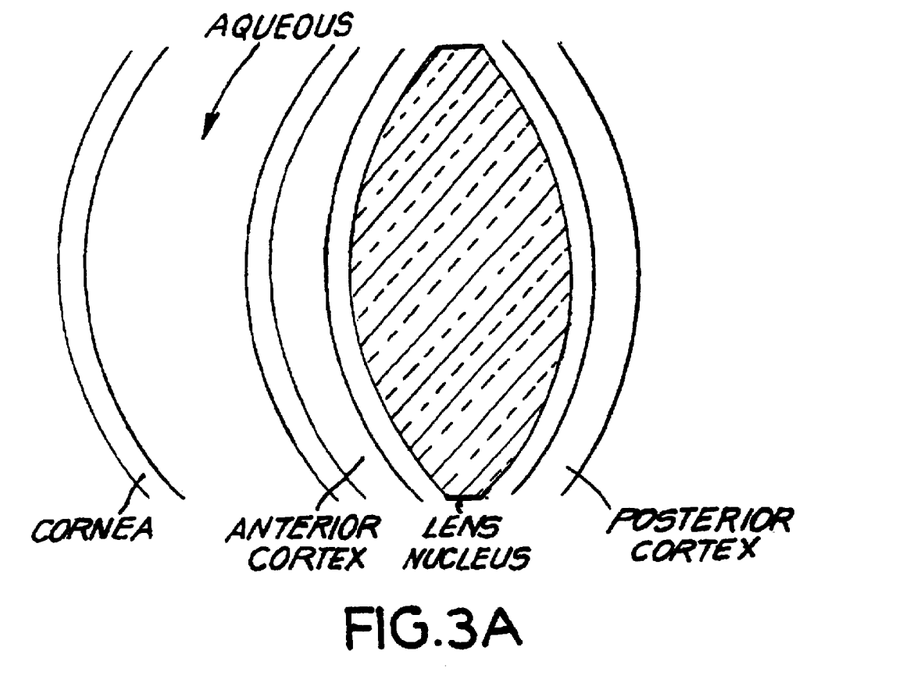
FIG. 3A is a schematic representation of a detailed scatter image of a cross-sectional portion of the eye shown in FIG. 1B, taken along line 2A—2A, representative of the central portion of the cornea and the crystalline lens.
Figure 3B:
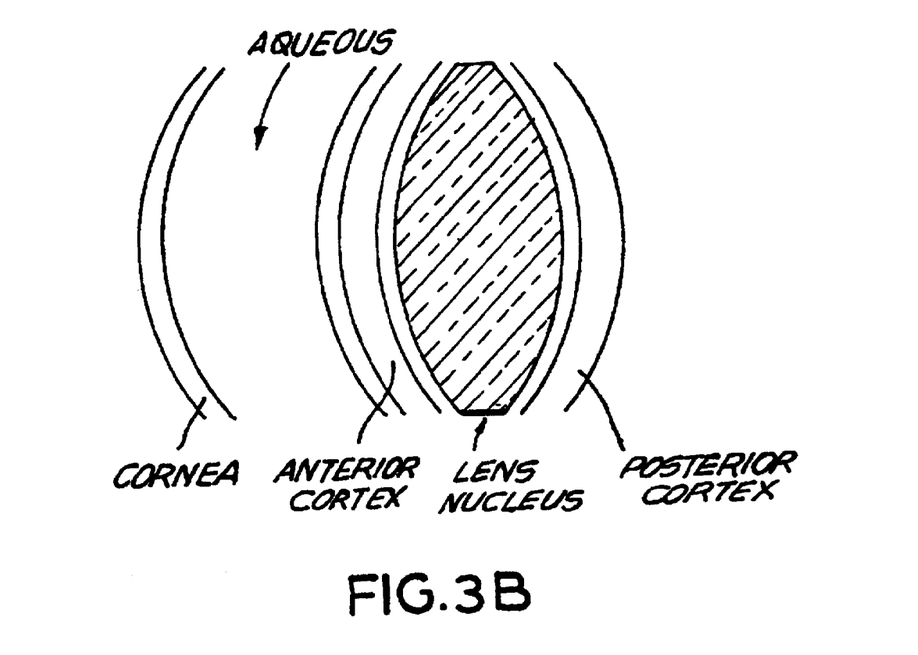
FIG. 3B is a schematic representation of a detected scatter image of a cross-sectional portion of the eye shown in FIG. 1B, taken along line 2B—2B, representative of an edge portion of the cornea and crystalline lens.
Figure 4:
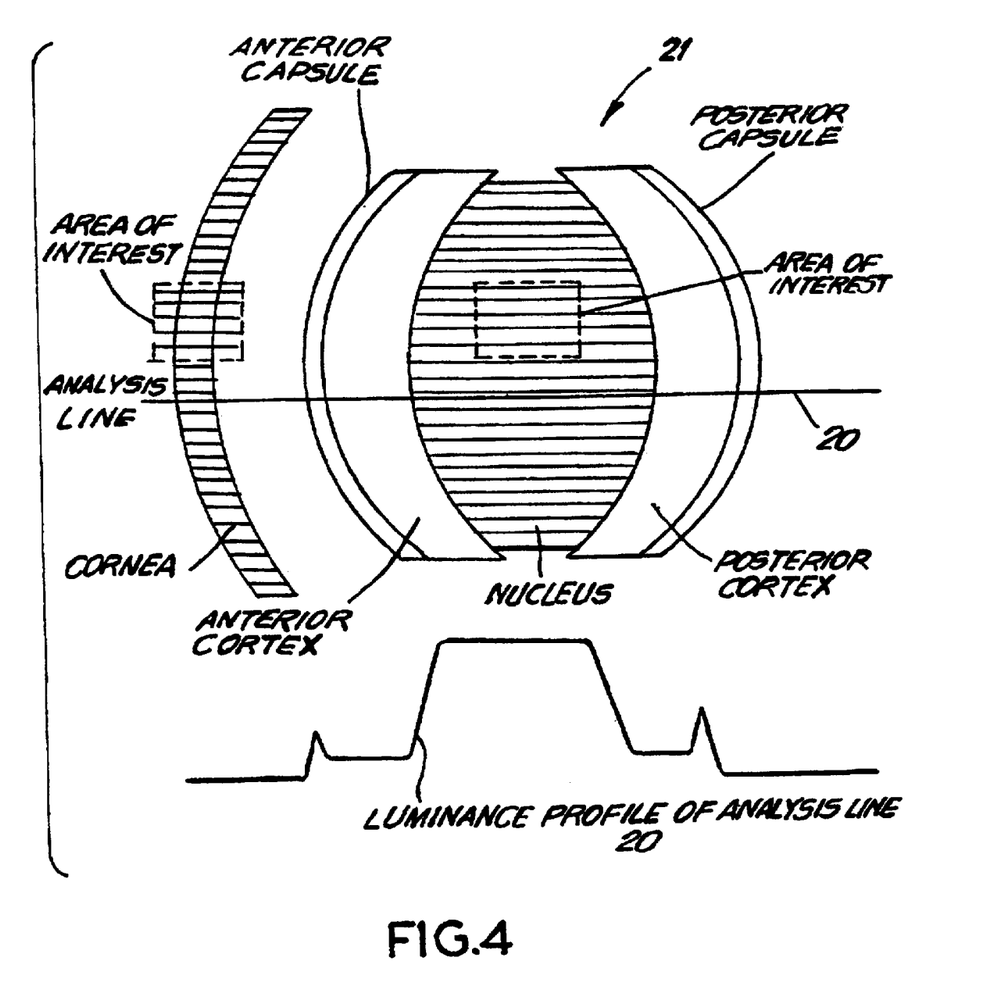
FIG. 4 is a schematic representation of a detected scatter image formed in accordance with the method of the present invention, illustrating the various ocular structures within the image and the use of digital image processing to provide the luminance (ie., optical density) profile along a selected line of analysis.
Figure 5:
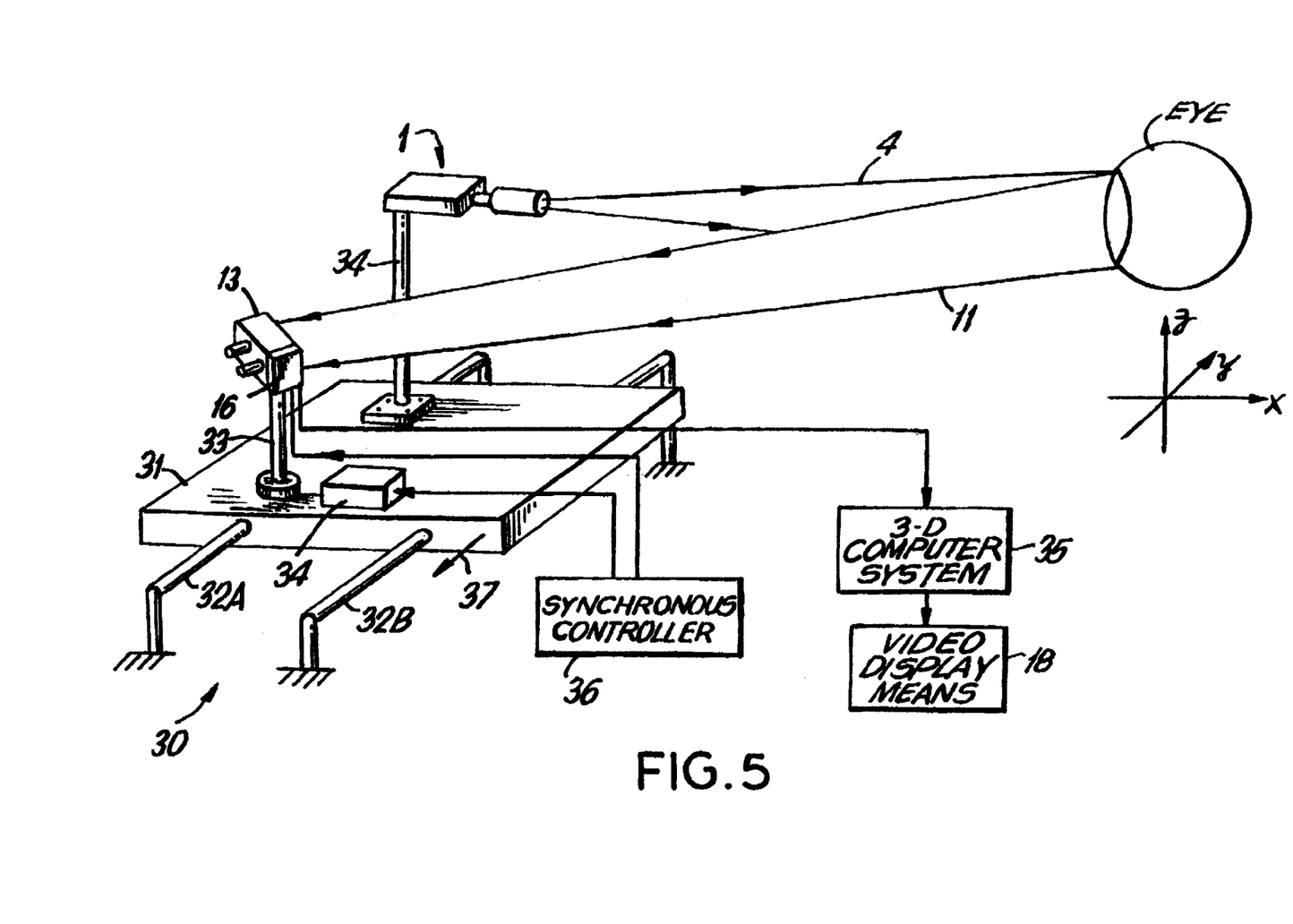
FIG. 5 is a schematic representation of the second embodiment of the apparatus of the present invention, realized as an ocular tissue analyzing system including a binocular microscope and scatter image detection and analyzing subsystem capable of forming a plurality of cross-sectional images of ocular tissue taken at different angles of illumination incidence, and reconstructing these cross-sectional images to form a three-dimensional image of the cornea, crystalline lens and surrounding ocular structures.
Figure 5A:
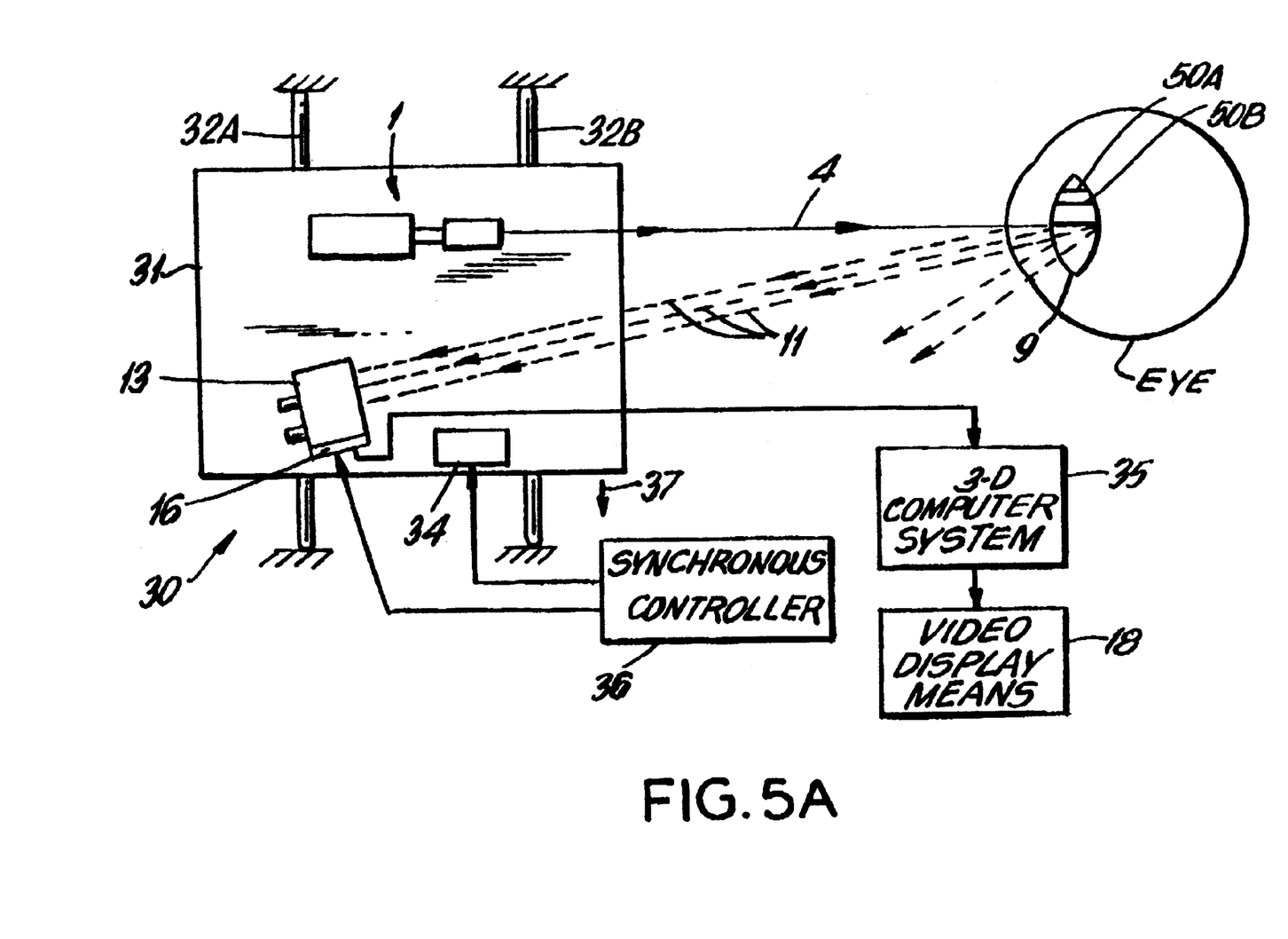
FIG. 5A is a schematic representation of the second embodiment of the apparatus of the present invention, as view from along X-Z plane of the coordinate reference system of FIG. 5.
Figure 6:
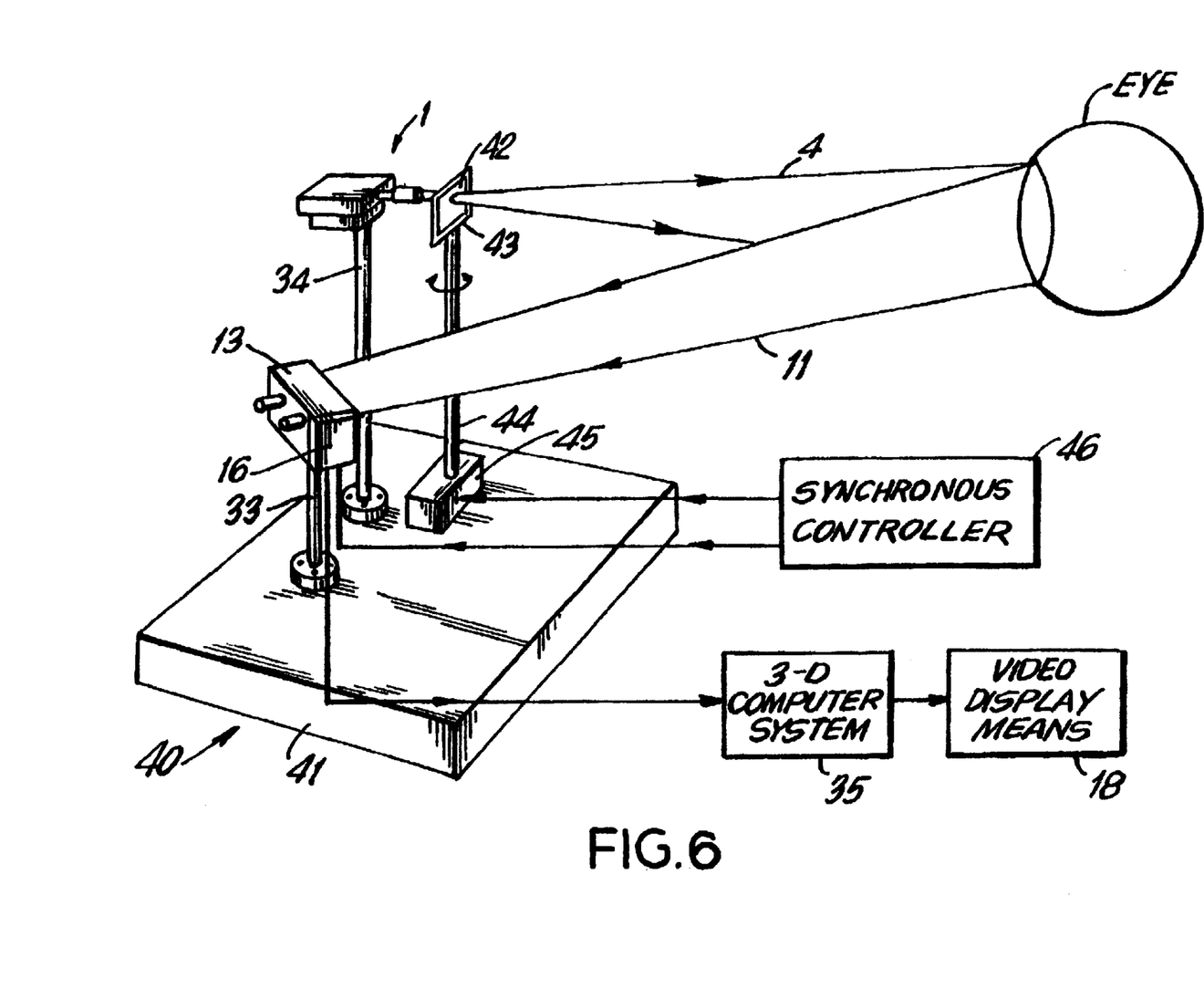
FIG. 6 is schematic representation of the third embodiment of the apparatus of the present invention, realized as an ocular tissue analyzing system including a binocular microscope and scatter image detection and analyzing subsystem capable of forming a plurality of cross-sectional images of the cornea and crystalline lens taken at different angles of illumination incidence, and reconstructing these cross-sectional images to form a three-dimensional image of the cornea and the crystalline lens.

Referring to FIGS. 1A and 1B in particular, the method of in vivo imaging ocular tissue according to the present invention, will first be described. According to the present invention, a laser beam is used to illuminate ocular tissue so that laser light scattered by molecules comprising the tissue can be detected on an image detection plane positioned at some preselected scatter angle. An essential characteristic of the illumination laser beam of the present invention is that it has a substantially planar configuration and a substantially uniform luminance over each slit-like cross-section. It has been discovered that by using a substantially planar laser beam having a substantially uniform luminance over each slit-like cross-section, wherein the width of each slit-like cross-section is substantially constant along the planar laser beam, it is possible to illuminate ocular tissue within the eye with a flux density which does not diverge along the depth of field, within which the largest depth dimension of the eye extends. Consequently, light scattered from ocular tissue anywhere along the propagation direction of the planar laser beam, will provide clear in-focus images detected at the image detection plane. Generation of a substantially planar laser beam in accordance with the principles of the present invention can be achieved using a commercially available zoom laser diode line projector system, such as Model V-SLM-S2Z from Newport Corporation of Mountain Valley, Calif. In general, the zoom laser-diode line projector system 1 comprises a line projector head 2 and a power supply 3. The line projector head 2 includes a 1.5 milliwatt laser, and electronic circuitry for regulation of optical power output and protection of the laser diode against line transients and electromagnetic noise. In addition to having an input for modulation of the laser output, line projector head 2 also includes beam shaping optics for structuring the optical distribution into a planar configuration. Mechanical movements are also provided for easy adjustment of the lens for planar beam geometry. Focus adjustment is also provided to allow the user to control the line width at any desired standoff. Line widths as narrow as 0.004 inch are achievable by adjustment of focus control, whereas line length is adjustable by controlling beam divergence. As illustrated in FIGS. 1A and 1B, in vivo imaging is achieved by directing at a preselected angle of incidence the essentially planar laser beam 4 through a cross-sectional portion of ocular tissue 6. In the example shown FIG. 1A, the ocular tissue comprises the crystalline lens, whereas in FIG. 1B the ocular tissue comprises cornea 7, anterior cortex 8, crystalline lens 9 and posterior cortex 10. As illustrated, incident planar laser beam 4 is directed along a line of incidence 50 to illuminate a cross-sectional portion (i.e., light scatter plane) 5 of the ocular tissue, thereby causing planar laser beam 4 to be scattered by molecules in that light scatter plane. Then, at some preselected angle of scatter, at least a portion of scattered laser light 11 is detected at an image detection plane 12 so as to form a cross-sectional image of the illuminated ocular tissue. As will be described in greater detail hereinafter, detection of the cross-sectional scatter image at image detection plane 12 can be achieved using one of a number of image detection techniques. In order to maintain the eye relatively stationary with respect to planar illumination beam 4 and image detection plane 12, the patient's head should be steadied by a conventional chin and forehead rest (not shown). In the steadied position, the patient faces the planar laser beam, which is oriented at about 45 degrees to the image detection axis, extending perpendicular from the image detection plane. As shown in FIG. 2, the scattered light is preferably focused through the optics of a binocular microscope system 13, so that the user can visualize the cross-sectional image formed under the illumination of planar laser beam 4. Also, as illustrated, a beam splitter 14 is provided along an optical path in binocular microscope system 13. The function of beam. splitter 14 is to split the beam of scattered light 11 from the cross-sectional portion of the cornea and crystalline lens, and direct the produced light beam 15 onto a photoelectronic image detector 16 to form a digitized cross-sectional image. Notably, scatter light beam 15 is focused by optics 16A to form the cross-sectional image on the image detection plane of image detector 16. Preferably, image detector 16 is a charged coupled device (CCD) video camera comprising an array of photoresponsive units, and is used in conjunction with a laser 2 producing a planar laser beam output having a wavelength preferably in the range of 600 to 650 nanometers. With this arrangement, a digitized cross-sectional image of the ocular tissue can be produced, while taking advantage of the CCD camera's sensitivity over this range of wavelengths. Also at the recommended power level of, for example, 1.5 milliwatts, the retina can be continuously exposed to the planar laser beam without risk of thermal injury. In such an embodiment, the digitized cross-sectional image consists of a plurality of pixels, each pixel having an intensity value. In a conventional manner, using a grey-scale of 0–255, the intensity of each pixel can be quantized with great precision, and so too the optical density of the ocular tissue represented by the pixel values comprising the image. In order to measure the optical density of ocular tissue, such as the crystalline lens, over particular zones of interest, the video output of CCD image detector 16 is provided to a conventional image processing computer 17 programmed with comprehensive image processing software that is capable of performing a variety of functions, including, for example, image analysis, image measurement and image processing. Such software is commercially available from Media Cybernetics, of Silver Springs, Md., under the trade name Image-Pro™. Image processing computer 17 also includes a video display device 18 for visually displaying the images acquired at the image detection plane of CCD camera 16. An example of several types of image analysis that would typically be performed upon the cross-sectional images, is illustrated in FIG. 4. As shown, in FIG. 4, digitized image 21 is displayed on video display device 18. A line of analysis 20 is selected, in this particular example, extending through the entire cross-sectional image 21 of the cornea, anterior cortex, the nucleus anc the posterior cortex of the crystalline lens. Then using the image analysis function of Image-Pro™ software, the luminance profile along the selected analysis line, can be determined and displayed. From the luminance profile, structural transitions and relative optical density in the ocular tissue can be readily discerned. By performing histographic analysis within selected areas of interest 22 in digitized cross-sectional image 21, it is possible to determine the optical density of certain portions of the patient's cornea and thus the precise degree and location of corneal haze. Notably, with a pixel grey scale of 0–255, optical density within ocular tissue can be quantified with the same degree of precision. Together with the constant luminance over each slit-like cross-section of the planar laser illumination beam 4 and the constant sensitivity of photoelectronic image detector 16, consistent cross-sectional images of ocular tissue can be produced and stored in a repeated manner without variation in the measurement of optical density. In this way, cross-sectional images of a patient's cornea, for example, can be produced, appropriately indexed as to location in the eye, and thereafter stored. At a subsequent date after, for example, exposure to corneal haze factors or suitable drug therapy for corneal haze, additional cross-sectional images can be produced at the same location within the cornea. Since the image formation conditions of the present invention can be maintained essentially constant during different image formation sessions, meaningful comparisons among these images can be made to determine the progress of the corneal haze. Also, owing to the constancy of the image formation conditions and the essentially non-diverging flux density along the width dimension of the planar illumination beam, images of the cornea along a number of parallel cross-sections can be formed, stored and compared to determine the location and degree of corneal haze in the cornea. By performing image measurement functions of Image-Pro™ software upon the detected cross-sectional image, the distances between and the areas and perimeters of various ocular structures can be precisely computed in a conventional manner using geometrical techniques. For a discussion on such measurements please see Systems of Ophthalmology, Vol. 5, Ophthalmic Optics and Refraction, p. 109, by Duke Elder, published by C V Mosby, St. Louis, 1970; and Clinical Visual Optics, p. 331, by Bennett and Rubbett, published by Buttersworth, London, 1984. Such measurements can be most useful in properly fitting a patient with an intracapsular intraocular lens that fits snugly into the capsular bag without the necessity of elastic haptics. With the method of the present invention, it is thus possible to precisely determine a patient's crystalline lens specifications, i.e., exterior and posterior curvature and diameter, thereby allowing the use of a new class of hapticless intraocular lenses. In order to produce a three-dimensional visual model of ocular tissue such as the cornea, either of the ocular tissue analyzing systems shown in FIGS. 5 and 6 can be used. In general, each system produces planar laser beam 4 for the purpose of illuminating, in a sequential manner, a plurality of parallel cross-sections of ocular tissue. As in the previously described embodiment, light scatter 11 from each cross-section is sequentially detected at the image detector plane, whereupon the detected image is stored or otherwise recorded. Thereafter, the plurality of cross-sectional images are reconstructed in a conventional computer graphics system having three-dimensional modeling capabilities. Two-dimensional views of the reconstructed model can then be examined along desired viewing directions provided by the computer graphics system. In FIG. 5, ocular tissue analyzing system 30 comprises a platform 31, which is adapted to move along a pair of spaced-apart rails 32A and 32B, which are fixed relative to a stationary base portion (not shown). Preferably, the base portion will be of a height sufficient to permit the user to view the eye through binocular microscope system 13 mounted above platform 31 by way of a first support stand 33. A stepper motor and an appropriate gearing mechanism 33A is provided for effectuating sequential movement of platform 31 relative to rails 32A and 32B and stationary base portion. As illustrated in FIG. 5, planar laser beam source I and binocular microscope system 13 of FIG. 2 are fixedly mounted to platform 31 by way of first and second support stands 33 and 34, respectively. Preferably, these support stands are adjustable so that the optical axes of laser beam source 1 and microscope system 13 can be adjusted to lie within substantially the same optical planes. Also, in this embodiment each selected line of incidence of the planar illumination beam and the scatter angle of the image detection plane are fixed at an angle of about 45 degrees. As in FIG. 2, microscope system 13 of FIGS. 5A and 5B also includes a beam splitter 14 for forming a light scatter beam which is directed onto photo-electronics image detector 16. As illustrated in FIGS. 5A and 5B, the output of image detector 16 is provided to conventional 3-D computer graphics system 35, which includes video monitor 18, as described hereinabove. A sequential controller 36 is also provided for synchronously controlling the movements of platform 31 with respect to stationary base, as well as for transferring detected images from image detector 16 to 3-D computer graphics system 35. At the beginning of an image acquisition process, platform 31 is positioned so that illumination beam 4 passes through a line of incidence 50A, co-planar with an end most portion of crystalline lens 9. During the first image acquisition cycle, planar laser beam 4 from source 1 is directed into the ocular tissue along line of incidence 50A which is substantially parallel to the optical axis of the eye. Along this line of incidence, planar laser beam 4 illuminates molecules lying along a light scatter plane coplanar with the planar laser beam and scatters the laser light. While under the control of synchronous controller 36, image detector 16 detects a portion of the scattered laser light which is focused through the optics of image detector 16 to form the scatter image. The scatter image is detected by image detector 16 which is positioned at a scatter angle which is fixed with respect to the selected line of incidence, along which planar laser beam 4 propagates. The detected scatter image is then transferred to 3-D computer graphics system 35 for storage. Synchronous controller 36 then moves platform 31 a very small lateral increment with respect to the eye, in the direction of the reference arrow 37. This lateral displacement permits planar laser beam 4 to be once again directed into the ocular tissue, but this time along a line of incidence 50B and within a light scatter plane which is offset, yet parallel to the previous line of incidence 50A and corresponding light scatter plane. The detected cross-section image along line of incidence 50B is then transferred from image detector 19 to 3-D computer graphics system 35 for storage. The above-described process of incrementally moving platform 31 to sequentially offset the line of incidence from the previous line of incidence and to synchronously acquire, transfer and store the detected image, is repeated a number of times under the control of synchronous controller 36 until a sufficient number of parallel cross-sectional images have been acquired. Thereafter, these images are used to compute one or more reconstructed three-dimensional image of the ocular structure under examination. Such 3-D image reconstructions can be produced using conventional programming techniques, then stored in memory of computer graphics system 35, and subsequently displayed along desired or selected viewing directions. The operation of ocular tissue analysis system 40 is similar in many respects to system 30 illustrated in FIGS. 5 and 5A. For example, laser source 1 and microscope system 13 are fixedly mounted onto a platform 41 in a manner described above in connection with the second embodiment. There are several differences, however. Platform 41 is stationary with respect to the eye of the patient. Also, to laterally displace planar laser beam 4 with respect to the patient's eye, a glass plate 42 of a predetermined thickness is mounted to a support frame 43. In turn, support frame 43 is supported by a post 44 which is rotatable with respect to platform 41 by a stepper motor 45 operated under the control of a synchronous controller 46. As stepper motor 45 is driven by synchronous controller 46, glass plate 42 is rotated a preselected amount, thereby effectuating desired incremental lateral displacement of the planar laser beam along a selected line of incidence, preferably parallel with the optical axis of the eye under examination. At the beginning of the image acquisition process, refractive plate 42 is preferably substantially perpendicular with planar illumination beam 4. During the first image acquisition cycle, the refractive plate 42 remains in its original or initial position, and the end most cross-section of ocular tissue is illuminated and the scatter image detected by image detector 16. After synchronously transferring the first detected image to the 3-D computer graphics system 35 under control of synchronous controller 46, refractive plate 42 is rotated by a small angular increment to displace slightly the line of incidence of planar illumination beam 4 away from the previously selected line of incidence. A cross-section of ocular tissue parallel to its first cross-section (ie., light scatter plane) is thus illuminated and the scattered light is detected by image detector 16, whereupon this second cross-sectional image is transferred to 3-D computer graphics system 35 for storage. The above image acquisition cycle is repeated a number of times under the control of synchronous controller 46 until a sufficient number of images are acquired for 3-D image reconstruction of the cornea of a particular patient, as discussed above. By performing image measurement functions upon the data represented in the 3-D image reconstruction (ie., model) of the cornea, several important types of data can be precisely obtained. For example, the thickness of the cornea at any point on the surfaces thereof can be computed and provided as digitized data output correlated with a point on the surface thereof. Also, topographical data regarding the surface characteristics of the patient's cornea (i.e. corneal curvature) prior to laser surgery can be precisely computed and provided as data output in a suitable format. Such corneal thickness data and topographical data can be then used by the ophthalmological surgeon in determining the new surface profile to be sculptured in the stroma tissue of the cornea of a particular patient, in order to achieve a desired degree of optical correction in his or her eye. Details regarding the computation of such types of data from 3-D image reconstructions of the cornea can be found in the publication entitled "Computerized Surface Reconstruction For Corneal Topography And Pachymetry Using Digitized Slit-Lamp Video Images", by J. H. Hoffinan, et al., Arvo Abstract Paper No. 1512-69 (1992). In the illustrated embodiments, photoelectronic image detecting apparatus and digital image processing techniques are utilized in carrying out the present invention. However, photographic image recording techniques and optical density measurement techniques for photographic images may also be used to carry out the present invention with expectedly good results.

The foregoing is described and claimed in my prior U.S. Pat. No. 5,404,884, the disclosure of which is incorporated herein by reference.

One improvement on the foregoing is an integrated unit that is hand-held. The platform and associated devices' mechanical movement of the light source or filter as described above provide a bulky and unwieldy apparatus for use in the field. According to this improvement thereon, the integrated hand-held unit 701 shown in FIG. 7A includes a "camera on a chip" or CCD, a laser, associated optics, and a means for presenting moving target to the patient. The recording apparatus in the hand-held unit includes a CCD (charge coupled device) chip on a circuit board with integrated optics; manufacturers of suitable CCD devices include Photobit (Pasadena, Calif.), Vision Ltd. (Edinburgh, Scotland), and Hewlett-Packard. A laser is directed from a temporal direction towards the nasal aspect of the eye; this avoids obstruction of the laser beam by the patient's nose, and shadows cast by the brow in patients with deep set eyes. The light reflected from the eye is captured by the CCD camera along the axis of the eye. While the CCD camera is positioned along the axis, the laser is preferably positioned to illuminate the eye at 45° towards the temporal aspect from the axis of the orbit.

Figures 7A, 7B:
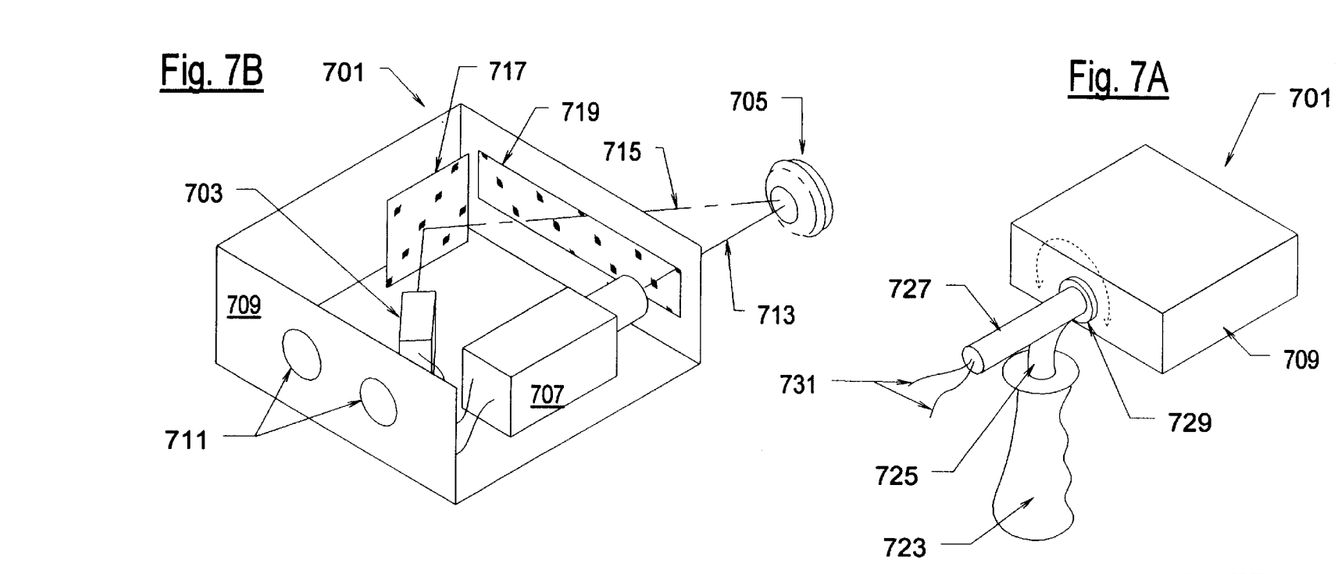
FIG. 7A is a rear perspective view of an improved apparatus according to this invention with an optional pistol grip.
FIG. 7B is an idealized partially exploded view of the improved apparatus.

FIG. 7B shows an idealized partially exploded view of the interior of such a handheld device. A laser 703 is directed towards a patient's eye 705. The laser light reflected from the eye is recorded on a video camera 707 (with associated optics and electronics), which may be a CCD. The housing 709 can include one or more ports 711 for connecting outside power to the device, and for connecting the output signal from the video camera to a display device (not shown). The video camera can output a signal to a display device such as a monitor (VDT) and/or a computer on which the digital (or digitized) video camera output signal is stored, or the camera may be a lens and associated fiber optics (like a fiber optic device used internally through a catheter) that is displayed on a monitor or recorded onto a video recorder (e.g., VCR). As shown, if the reflected beam 713 is considered coaxial with the axis of the eye, then the incident beam 715 is 45° therefrom, and is facilitated in coming from this direction by means of a reflecting device 717 such as a mirror; micromirrors (e.g., etched onto chips) have been described in the literature and such are useful herein as the reflecting device.

Figure 7C:
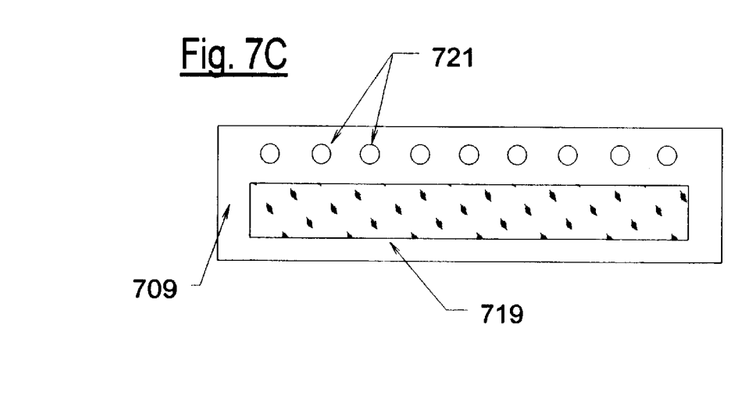
FIG. 7C is an idealized front view of the improved device showing a series of lamps.

Unlike the larger models described above, the present improvement is intended for use in the field and so is much smaller. According, different methods for scanning the laser across the desired field of view must be considered. One method is shown in FIG. 7C, an idealized front view of the device, in which a window 719 is shown for the laser beams to pass through. Positioned "above" the window are a series of lamps 721, which can be light emitting diodes (LEDs). When the device is positioned correctly, the patient is instructed to view the series of LEDs; electronic circuitry well known (and not shown) is used to light the lamps in a relatively slow sequence; the patient is instructed to follow the sequence as one LED at a time lights. Thus, the patient's eye is caused to move laterally, and so the eye is effectively scanned by the laser beam.

As noted above, the laser is preferably directed from the temporal aspect to minimize expected problems with shadows and obstructions. As shown in FIG. 7B, the device is positioned for examining a patient's right eye. To examine the left eye while keeping the device in the same orientation as shown, the nose would cause an obstruction. In one embodiment, the device is simply flipped upside down, rotated about the axis of the orbit, so that the laser is on the other side of the video camera (i.e., from the right temporal aspect when compared with FIG. 7B). In another embodiment, as shown in FIG. 7A, the device can be rotatably supported by a grip. For example, a pistol grip 723 is attached by arm 725 to barrel 727, which is rotatably mounted to the case by a flange assembly 729. The barrel is preferably a conduit for leads 731 through which the video output and power input leave and enter the device. As shown by the dotted line, the device is rotated about the barrel (defining an axis essentially parallel with the optic axis of the eye) to switch from one eye to the other.

Figure 7D:
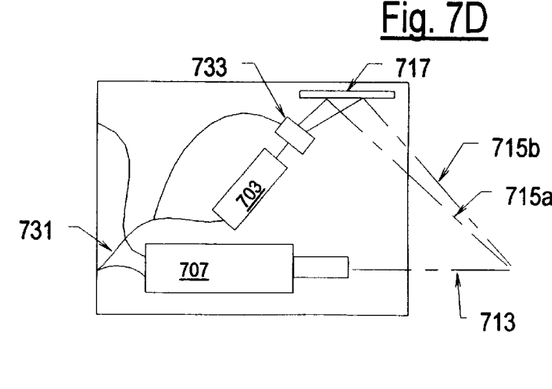
FIG. 7D is an idealized overhead view of the interior of another improved device.

Instead of the LEDs, another method for scanning the laser beam across the patient's eye is to manipulate the beam electrooptically. FIG. 7D shows an idealized top view of the interior of the device, similar to the perspective view shown in FIG. 7B. Here, the power supply wires 731 power the laser 703, the camera 707, and an scanning device 733. The scanning device can be a piezoelectric crystal that changes its index of diffraction as a function of the voltage difference across its faces; accordingly, the power supply wires are needed, and the box indicated at 733 requires associated electronics. Still another method for scanning the laser beam is by the use of prisms, such as disclosed by U.S. Pat. No. 5,227,910 (the disclosure of which is incorporated herein by reference). Yet another method for scanning the laser is to use methods such as used in hand-held laser-scanning bar code readers; for example, a rotating mirror as described in U.S. Pat. No. 5,146,463 (the disclosure of which is incorporated herein by reference), for this invention, the mirror needs to rotate more slowly than in a bar code scanning reader.

As described, this invention is suitable for imaging tissue in the anterior portion of the eye. Such ocular tissue includes, for example, the cornea, the anterior chamber of the eye (i.e., where the aqueous humor is contained), the iris, and the crystalline lens. Thus, this device is useful, among other analyses, for screening patients for cataracts.

One of the advantages of the present system is that is it portable and simple to use, and with suitable software as mentioned above, is quick to use for accurate diagnosis. For example, assume the device has a series of LEDs that are sequentially lit to cause the patient to move his eye. Because a CCD can acquire images at a very rapid rate, if one of the frames (images) acquired by the CCD is not aligned with the others (as determined by the software), that frame can be eliminated from the processing.

While the particular embodiments shown and described above have proven to be useful in many applications in the ophthalmic art, further modifications of the present invention herein disclosed will occur to persons skilled in the art to which the present invention pertains, and all such modifications are deemed to be within the scope and spirit of the present invention defined by the appended claims.

What is claimed is:

1. An apparatus for in vivo imaging of anterior ocular tissue in the eye of a patient, said apparatus comprising:
    laser means for providing a laser beam having a substantially planar configuration in a direction towards said eye;
    camera means for detecting light from said laser reflected by said ocular tissue;
    a housing for containing said laser means and said camera means, said housing comprising a window that allows transmission of said laser beam towards the eye for and of said light reflected by said tissue back to said camera, and at least one port for communication of power and data signals to and from said camera and laser means; and
    moving target means attached to said housing for providing a target on which said patient can fixate with said eye and which target is caused to move laterally.

2. The apparatus of claim 1, wherein the moving target means is a series of lamps.

3. The apparatus of claim 1, further comprising a grip attached to said housing.

4. The apparatus of claim 3, wherein said grip is attached to the housing by a barrel that defines an axis essentially parallel with the optical axis of said eye, and wherein said barrel is attached rotatably to said housing.

5. The apparatus of claim 4, wherein the apparatus is hand-held.

6. The apparatus of claim 1, further comprising means for connecting said apparatus to a display device and means for displaying images captured by said camera at said display device.

7. An apparatus for in vivo imaging of ocular tissue in the anterior portion of the eye of a patient, said apparatus comprising:
    laser means for providing a laser beam suitable for imaging having a substantially planar configuration in a direction towards said eye;
    camera means for detecting light from said laser reflected by said ocular tissue;
    a housing for containing said laser means and said camera means, said housing comprising a window that allows transmission of said laser beam towards the eye for and of said light reflected by said tissue back to said camera, and at least one port for communication of power and data signals to and from said camera and laser means; and
    laser scanning means for effecting a lateral scan of the laser beam across the patient's eye.

8. The apparatus of claim 7, wherein the camera is a charge coupled device.

9. The apparatus of claim 7, wherein the apparatus is hand-held.

10. The apparatus of claim 7, wherein said laser scanning means comprises a piezoelectric crystal, a prism, a rotating mirror, directional micromirrors, or a combination thereof.

11. A method for in vivo imaging of ocular tissue in the anterior portion of the eye of a patient, said apparatus comprising:
    providing a laser beam suitable for imaging having a substantially planar configuration in a direction towards said eye;

detecting light from said laser reflected by said ocular tissue;

providing housing for containing: a laser to generate said laser beam and a camera to detect said light, a window that allows transmission of said laser beam towards the eye for and of said light reflected by said tissue back to said camera, and at least one port for communication of power and data signals to and from said camera and laser means; and effecting a lateral scan of the laser beam across the patient's eye; and receiving and processing light reflected by said corneal tissue to generate said image of ocular tissue.

12. The apparatus of claim 1, wherein the ocular tissue is the cornea.

13. The apparatus of claim 1, wherein the ocular tissue is the crystalline lens.

14. The apparatus of claim 7, wherein the ocular tissue is the cornea.

15. The apparatus of claim 7, wherein the ocular tissue is the crystalline lens.

16. The method of claim 11, wherein the ocular tissue is the cornea.

17. The method of claim 11, wherein the ocular tissue is the crystalline lens.

* * * * *